United States Patent
Bhogal

(10) Patent No.: US 11,717,304 B2
(45) Date of Patent: Aug. 8, 2023

(54) METHODS AND APPARATUS FOR INCREASING CEREBRAL BLOOD FLOW

(71) Applicant: Pervinder Singh Bhogal, London (GB)

(72) Inventor: Pervinder Singh Bhogal, London (GB)

( * ) Notice: Subject to any disclaimer, the term of this patent is extended or adjusted under 35 U.S.C. 154(b) by 780 days.

(21) Appl. No.: 16/604,636

(22) PCT Filed: Apr. 13, 2018

(86) PCT No.: PCT/EP2018/059589
§ 371 (c)(1),
(2) Date: Oct. 11, 2019

(87) PCT Pub. No.: WO2018/189391
PCT Pub. Date: Oct. 18, 2018

(65) Prior Publication Data
US 2021/0113214 A1    Apr. 22, 2021

(30) Foreign Application Priority Data

Apr. 13, 2017 (GB) .................................... 1706001
Jul. 10, 2017 (GB) .................................... 1711070
Mar. 5, 2018 (GB) .................................... 1803537

(51) Int. Cl.
*A61B 17/135*    (2006.01)
*A61B 5/026*    (2006.01)
(Continued)

(52) U.S. Cl.
CPC .......... *A61B 17/1355* (2013.01); *A61B 5/026* (2013.01); *A61B 5/6824* (2013.01); *A61B 5/6828* (2013.01); *A61B 2017/00022* (2013.01)

(58) Field of Classification Search
CPC ... A61B 17/1355; A61B 5/026; A61B 5/6824; A61B 5/6828; A61H 1/00; A61H 23/04; A61H 2011/005; A61H 2201/0103
See application file for complete search history.

(56) References Cited

U.S. PATENT DOCUMENTS

2005/0075531 A1    4/2005  Loeb et al.
2008/0015478 A1*   1/2008  Bose ..................... A61H 23/04
                                                          601/152
(Continued)

FOREIGN PATENT DOCUMENTS

EP      2074981 A1    7/2009
WO   2016033339 A1    3/2016
WO   2017117305 A1    7/2017

OTHER PUBLICATIONS

International Search Report and Written Opinion for International Application No. PCT/EP2018/059589, dated Oct. 24, 2018, 17 pages.

(Continued)

*Primary Examiner* — Amanda K Hulbert
*Assistant Examiner* — Philip C Edwards
(74) *Attorney, Agent, or Firm* — RatnerPrestia

(57) ABSTRACT

Methods and apparatus for increasing cerebral blood flow for improving the flow of blood to the brain during and/or following an ischaemic stroke. The apparatus includes a plurality of inflatable cuffs to be positioned, in use, around a respective limb of a patient. Once inflated, the cuffs exert a pressure upon the limb to reduce blood flow to the limb below the point at which the cuff is positioned. Reducing blood flow to the limbs causes an increase in blood flow to the brain, and will therefore improve stroke outcomes. The apparatus includes a control module for controlling inflation and deflation of each cuff. The control module detects, measures and monitors cerebral blood flow and uses these measurements to control inflation and deflation of each cuff such that cerebral blood flow is maintained above a baseline level during treatment of the patient.

19 Claims, 1 Drawing Sheet

(51) Int. Cl.
*A61B 5/00* (2006.01)
*A61B 17/00* (2006.01)

(56) References Cited

U.S. PATENT DOCUMENTS

2009/0287069 A1* 11/2009 Naghavi ............ A61B 17/1355
   128/898
2010/0105993 A1   4/2010 Nghavi et al.
2015/0094755 A1* 4/2015 Hong ................. A61B 5/02225
   606/202

OTHER PUBLICATIONS

Demchuk et al., "Accuracy and Criteria for Localizing Arterial Occlusion With Transcranial Doppler", Journal of Neuroimaging, vol. 10, No. 1, 2000, 12 pages.

Demchuk et al., "Specific Transcranial Doppler Flow Findings Related to the Presence and Site of Arterial Occlusion", 2019, downloaded from http://ahajournals.org, pp. 140-146.

Rathakrishnan et al., "Validation of Transcranial Doppler with CT Angiography in Cerebral Ischaemia: A Preliminary Pilot Study in Singapore", Annals Academy of Medicine, 2008, vol. 37, No. 5, pp. 402-405.

Schlachetzki et al., "Transcranial Ultrasound from Diagnosis to Early Stroke Treatment—Part 2: Prehospital Neurosonography in Patients with Acute Stroke—The Regensburg Stroke Mobile Project", Cerebrovascular Diseases, 2012, vol. 33, pp. 262-271.

Thorpe et al., "Decision Criteria for Large Vessel Occlusion Using Transcranial Doppler Waveform Morphology", Frontiers in Neurology, 2018, vol. 9, Article 847, 10 pages.

Tsivgoulis et al., "Validation of Transcranial Doppler With Computed Tomography Angiography in Acute Cerebral Ischemia", Stroke, https:///www.strokeaha.org, 2007, pp. 1245-1249.

Wilson et al., "Stroke at High Altitude Diagnosed in the Field Using Portable Ultrasound", Wilderness & Environmental Medicine, 2011, vol. 22, pp. 54-57.

International Preliminary Report on Patentability for International Application No. PCT/EP2018/059589, dated Oct. 15, 2019, 12 pages.

\* cited by examiner

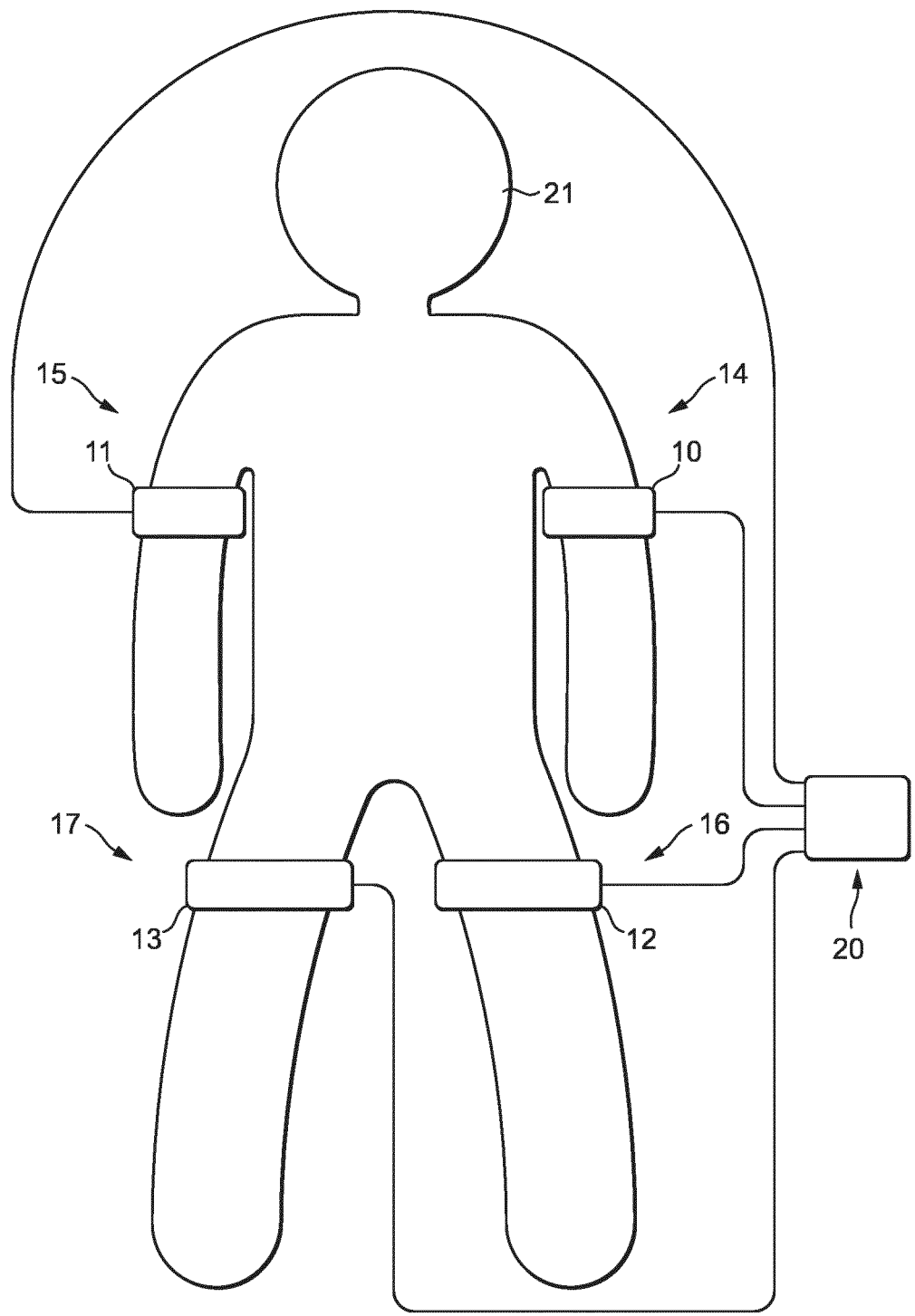

METHODS AND APPARATUS FOR INCREASING CEREBRAL BLOOD FLOW

TECHNICAL FIELD OF THE INVENTION

The present invention relates to methods and apparatus for increasing cerebral blood flow, in particular for improving the flow of blood to the brain during and/or following ischaemic strokes and other events, such as delayed cerebral vasospasm after sub-arachnoid haemorrhage, reversible cerebral vasospasm syndrome or any disease that can restrict an adequate amount of blood reaching the target tissue.

BACKGROUND OF THE INVENTION

An acute ischemic stroke is characterised by the sudden loss of blood circulation to an area of the brain, resulting in corresponding loss of neurological function. This loss of blood flow to the brain occurs when an artery becomes blocked by the formation of a blood clot, either within the brain (cerebral thrombosis) or elsewhere (embolism) or in the case of cerebral vasospasm when the artery is severely narrowed, which can also occur in other similar conditions such as reversible cerebral vasospasm syndrome. When the principal cerebral blood flow fails, such as in the case of an ischemic stroke, a subsidiary network of vascular channels operates to try to stabilise cerebral blood flow. This subsidiary network is formed of cerebral collaterals. Collateral status differs among patients with acute ischemic stroke and poor collaterals are a strong predictor of poor neurological outcome after a stroke. The goal of any acute treatment of a stroke, therefore, is to restore blood flow to the part of the brain affected by the blockage as quickly as possible, to improve the outcome for the patient.

In one such treatment, an aortic occlusion device has been designed to be inserted into the abdominal aorta of a patient to divert blood flow from the lower extremities to the brain, and improve the circulation of the hypoxic brain tissue by increasing cerebral collateral circulation, in patients with acute ongoing stroke. The device aims to increase delivery of oxygenated blood to the stroke's ischemic penumbra, the area of the brain that, despite lacking oxygen, is not dead but will continue to progress to cellular death, if a blood supply is not restored. The ability to salvage that penumbra and minimise the size of the infarcted area may lead to improved neurological recovery. The device, developed by CoAxia and known as NeuroFlo Technology, has shown promising results in randomised trials (SENTIS—Safety & Efficacy of NeuroFlo Technology In Ischemic Stroke).

It will be immediately appreciated, however, that this treatment requires a surgical procedure—inserting the device into the aorta. The treatment is, therefore, not without risks and may not be readily available as an early intervention technique to restore cerebral blood flow. Accordingly, there is a need for an additional method of improving cerebral blood flow in order to maximise the chances of a good neurological recovery after a stroke. The present invention aims to address this need by providing a non-surgical stroke treatment suitable for early intervention, such as in the case of an emergency, by paramedics, for example.

SUMMARY OF THE INVENTION

In its broadest sense, the present invention provides an apparatus comprising a plurality of cuffs, each cuff being inflatable and deflatable, and each cuff being positionable, in use, around a respective limb of a patient and inflatable to exert a pressure upon the limb sufficient to reduce blood flow to the limb below the point at which the cuff is positioned; and a control module, to which the cuffs are attachable, the control module comprising a pump with which each cuff is in fluid communication and a valve arrangement associated with each cuff to control flow of fluid to and from each cuff; wherein the control module is adapted to inflate and deflate each cuff independently of the others.

More particularly, the present invention provides an apparatus for maintaining cerebral circulation in a patient above a baseline flow rate during treatment, the apparatus comprising: (a) a plurality of compression cuffs, each cuff being inflatable and deflatable and each cuff being positionable, in use, around a respective limb of a patient and inflatable to exert a pressure upon the limb sufficient to reduce limb blood flow below the point at which the cuff is positioned; (b) a control module to which the cuffs are attachable, the control module comprising a pump with which each cuff is in fluid communication and a valve arrangement associated with each cuff to control flow of fluid to and from each cuff, the control module being adapted to inflate and deflate each cuff independently of the others; and (c) a cerebral blood flow monitoring apparatus adapted to detect the baseline flow rate in the cerebral circulation and to repeatedly measure or continuously monitor flow rate in the cerebral circulation during treatment of the patient, wherein the control module is in operative communication with the cerebral blood flow monitoring apparatus, such that the control module is adapted to inflate one or more cuffs to reduce the respective limb blood flow below the point around the respective limb at which the inflated cuff or each inflated cuff is positioned and maintain inflation of the or each cuff for a predetermined period, to thereby elevate the cerebral circulation from the baseline flow rate to an increased flow rate, and thereafter control inflation of the plurality of cuffs to maintain the measured or monitored flow rate above the baseline flow rate during treatment, by reducing limb blood flow and augmenting cerebral circulation.

The reference to reducing blood flow to the limb below the point at which the cuff is positioned will be understood as referring to reducing blood flow in that part of the limb (to which the cuff is positioned) remote the head of the patient.

In one embodiment, the control module is configured to deflate each cuff sequentially for a plurality of release periods, the release periods being intermittent during the predetermined period.

Conveniently, the fluid is air.

Preferably, the cerebral blood flow monitoring apparatus is further adapted to detect flow direction in the cerebral circulation.

Preferably, the cerebral blood flow monitoring apparatus is adapted to measure cerebral circulation in both anterior and posterior circulation.

Preferably, the control module further comprises an imaging device adapted to determine where an occlusion is present in the cerebral circulation.

Preferably, the cerebral blood flow monitoring apparatus is adapted to determine cerebral blood flow rate in cerebral collateral arteries.

Preferably, each cuff is independently inflatable to a determined pressure, which pressure may be the same as or different from each other cuff or all other cuffs.

Preferably, the control module includes a sensor to determine the number of cuffs attached to the control module.

Preferably, each cuff comprises a blood flow sensor to determine whether, in use, blood is flowing through the limb of the patient adjacent the cuff.

Suitably, the apparatus comprises four cuffs.

In one embodiment, the control module is configured to inflate each of the plurality of cuffs simultaneously to restrict blood flow to each limb for a first predetermined period. Ideally, the first predetermined period is less than the time for limb occlusion, which is about 6 hours. Preferably, the control module is configured to deflate at least one cuff after the first predetermined period. More preferably, the control module is configured to deflate a first cuff after the first predetermined period and a second cuff after a second predetermined period, wherein the first cuff is re-inflated after the first predetermined period. Preferably, the second predetermined period is less than the time for limb occlusion.

In another embodiment, the control module is configured to control flow of fluid to and from the cuffs following a cyclical routine, each cycle of the routine comprising a series of steps of inflating all of the cuffs apart from one cuff to increase the cerebral circulation from the baseline flow rate to the increased flow rate and maintaining this configuration for a release period; and repeating this step for each of the plurality of cuffs in turn such that each cuff is deflated in turn and is maintained in a sufficiently-deflated state to allow blood flow to the respective limb whilst the other cuffs are configured in a sufficiently-inflated state to reduce limb blood flow.

In a further embodiment, the control module is configured to inflate each cuff simultaneously for a first predetermined period, with intermittent release of pressure in each cuff for a plurality of release periods to temporarily allow blood flow to the limbs during the first predetermined period.

In preferred embodiments, the apparatus further comprises a heart rate sensor. More preferably, the control module of the apparatus controls the cuffs to inflate with cardiac gating, in time with contraction of the heart ventricles, in response to an output from the heart rate sensor.

In further preferred embodiments, the apparatus further comprises a cerebral blood flow monitoring apparatus; or is formed as a system comprising an apparatus as described above and further comprising a cerebral blood flow monitoring apparatus in communication with the control module of the apparatus.

Suitably, the cerebral blood flow monitoring apparatus uses: i) ultrasound and transcranial Doppler; ii) infra-red sensing; and/or iii) computed tomography and/or magnetic resonance imaging. However, other devices for monitoring blood flow will be suitable for use in the present invention.

Preferably, the control module further comprises a feedback module paired to the cerebral blood flow monitoring apparatus and providing regular or continuous monitoring of the cerebral circulation such that the control module provides automatic adjustment of cuff inflation to maintain optimal cerebral circulation as close to normal circulation as possible.

In a further aspect, the present invention provides methods for increasing cerebral blood flow in a patient during treatment.

In one embodiment, the method comprises limiting blood flow to at least one limb of the patient for a predetermined period using at least one pressure cuff.

More specifically, the method preferably comprising the steps of: (i) detecting and measuring a baseline cerebral blood flow of the patient; (ii) generating a reduced blood flow to each limb of the patient other than a first limb and allowing blood to flow to the first limb for a release period; generating a reduced blood flow to the first limb and allowing blood flow to a second limb for the release period; and sequentially repeating for each limb the steps of allowing blood flow to one limb whilst generating a reduced blood flow to the other limbs, thereby increasing the cerebral circulation from a baseline flow rate to an increased blood flow rate; (iv) monitoring the increased cerebral blood flow rate to determine an optimum treatment sequence, the optimum treatment sequence being a pattern of reducing and releasing limb blood flow that provides an increase in cerebral blood flow from the baseline cerebral blood flow; and (v) using the optimum treatment sequence to maintain the cerebral blood flow at an increased level, relative to the baseline blood flow rate, throughout treatment of the patient.

Alternatively, the method comprises (i) detecting and measuring a baseline cerebral blood flow of the patient; (ii) generating a restricted limb blood flow to at least one limb of the patient using at least one cuff that is inflatable and deflatable; (iii) detecting and measuring a treatment cerebral blood flow in response to the restricted limb blood flow and maintaining the restricted limb blood flow until the treatment cerebral blood flow is higher than the baseline cerebral blood flow; and (iv) monitoring the treatment cerebral blood flow throughout treatment of the patient and controlling inflation and deflation of the at least one cuff such that a treatment cerebral blood flow higher than the baseline blood flow rate is maintained throughout treatment of the patient.

In a preferred embodiment, cerebral blood flow of the patient is monitored to provide feedback on the effectiveness of the at least one pressure cuff at increasing cerebral blood flow. Ideally, the feedback is used to determine the extent to which limb blood flow is limited, and/or the overall duration of limb blood flow limitation.

Preferably, the method comprises generating a reduced limb flow to each limb of a patient for a predetermined period.

Suitably, blood is allowed to flow to each limb simultaneously for a plurality of release periods, the release periods being intermittent during the predetermined period.

Optionally, limiting blood flow comprises cutting off blood flow to the limb. Suitably, the predetermined period is up to 6 hours.

Alternatively, limiting blood flow comprises reducing but not cutting off blood flow. Suitably, the predetermined period is greater than 6 hours.

The predetermined period may be repeated as necessary during a treatment.

Suitably, the release period is between about one and twenty minutes.

Preferably, the release period is at least about two minutes.

Preferably, the release period is up to about five minutes.

Preferably, the release period is about two to three minutes.

Suitably, the patient is a patient having a need for an increased cerebral blood flow.

In a preferred embodiment, the method is achieved by use of the above-described apparatus for limiting blood flow to the limbs.

In a further aspect, the present invention provides the use of an apparatus as described above in a method as described above.

BRIEF DESCRIPTION OF THE DRAWINGS

The above and other aspects of the present invention will now be described in further detail, by way of example only, with reference to the accompanying drawing in which:

FIG. 1 schematically illustrates an embodiment of the apparatus of the present invention applied to a patient and comprising four inflatable pressure cuffs.

DETAILED DESCRIPTION OF THE PREFERRED EMBODIMENTS OF THE INVENTION

In general terms, the apparatus and method of the present invention operate by inflating cuffs attached to an upper portion of each of the limbs of the patient to limit the blood flow to each limb for a predetermined period. Blood flow can either be fully or partially occluded. Where blood flow to a limb is cut off completely, the time for limb occlusion is generally up to about 6 hours. However, if blood flow is reduced, rather than cut off, the time to limb occlusion can be extended. The overall aim of the apparatus and method of the present invention is to divert as much blood as possible to the collaterals of the brain of a patient until clinicians can remove a blockage that is preventing principal blood flow to the brain.

This aim is achieved using a system of pressure cuffs, adapted for use in a number of ways. For example, blood flow to all of the patient's limbs can be cut off for a predetermined period to maximise blood flow to the cerebral collaterals for that period. Alternatively, blood flow to all of the limbs can be reduced, diverting less blood to the cerebral collaterals but nevertheless providing increased blood flow to the cerebral collaterals, whilst blockages are removed. Other alternatives include reducing or cutting off blood flow to one or more limbs for a predetermined period but providing for short release periods of normal blood flow intermittently during the predetermined period, to allow the limbs some recovery time before blood flow is again reduced or cut off.

With reference to FIG. 1, the apparatus comprises four pressure cuffs 10, 11, 12, 13. The cuffs are of a generally standard construction as used in medical apparatus, such as sphygmomanometers, and include a transducer or other sensor to determine the presence or absence of blood flow (pulse) through the cuff. Cuffs 10, 11, 12, 13 are dimensioned to fit a respective limb 14, 15, 16, 17 and are attached, in use, towards the upper portion thereof, adjacent the torso, in order to achieve maximum effect. That is to say, each cuff 10, 11, 12, 13 is attached to an upper thigh or an upper arm. Typically, cuffs 10, 11, 12, 13 are inflated to apply a pressure to the limb at just above the systolic pressure. However, lower pressures may suffice and a pressure below systolic pressure will be sufficient to divert flow away from the limb and to the brain.

In a preferred embodiment, once each of cuffs 10, 11, 12, 13 is inflated, the pressure in a first cuff 10 is reduced for a short release period, suitably around two to three minutes, to allow normal blood flow to respective limb 14. At the end of the release period, the pressure to first cuff 10 is increased again to re-reduce the blood flow, whilst the pressure to a second cuff 11 is reduced to allow normal blood flow to its associated limb 15 for the release period. The apparatus cycles through this procedure for each cuff 10, 11, 12, 13 in turn, thereby limiting aggregate blood flow to limbs 14, 15, 16, 17, but without reducing blood flow to each individual limb 14, 15, 16, 17 to levels at which tissue damage to the limb will occur.

By limiting blood flow to limbs 14, 15, 16, 17, blood flow is diverted to the brain 21, to enhance circulation to the cerebral collaterals. Collateral circulation maintains a degree of blood flow to the brain while the clinicians treating the patient treat the blood clot that is disrupting the principal blood supply to brain 21, in the event of a stroke. Additionally, the same procedure will trigger mechanisms collectively referred to as 'ischaemic conditioning', thought to be useful for the treatment of other conditions such as cerebral vasospasm, atherosclerosis and preventing strokes after mini-strokes (transient ischaemic attacks—TIAs).

The apparatus further includes a control module 20. Cuffs 10, 11, 12, 13 are attachable to control module 20 and control module 20 includes sensors to determine the number of cuffs 10, 11, 12, 13 attached. Consequently, control module 20 is able to control inflation and deflation to fewer than all four cuffs 10, 11, 12, 13 if appropriate. For example, where the patient has fewer than four limbs or where clinical considerations dictate that blood flow to a particular limb should not be moderated, such as in the case of limb damage where it may be preferable for blood flow not to be constricted whilst treatment to the limb is undertaken; or if drugs are being administered via a particular limb; or if arterial access is required for a mechanical thrombectomy procedure, for example.

Control module 20 is adapted to inflate and deflate each cuff 10, 11, 12, 13 independently. The skilled person will be readily able to determine suitable air pump and valves mechanisms, and electrical control circuits and control mechanisms.

To illustrate operation of control module 20 during use of the apparatus and method of the present invention, an example cyclical routine is:

(i) Module 20 inflates cuffs 11, 12, 13 to a level to restrict blood flow to limbs 15, 16, 17 respectively. Ideally the cuffs are inflated to a pressure just above systolic pressure. Module 20 deflates cuff 10 to a level to allow blood flow to limb 14.

(ii) After 2 minutes, module 20 inflates cuff 10 to restrict blood flow to limb 14. At the same time, module 20 deflates cuff 11 to allow blood flow to limb 15. Cuffs 12, 13 remain inflated to restrict blood flow to limbs 16, 17 respectively.

(iii) After a further 2 minutes, module 20 inflates cuff 11 to restrict blood flow to limb 15. At the same time, module 20 deflates cuff 12 to allow blood flow to limb 16. Cuffs 10, 13 remain inflated to restrict blood flow to limbs 14, 17 respectively.

(iv) After a further 2 minutes, module 20 inflates cuff 12 to restrict blood flow to limb 16. At the same time, module 20 deflates cuff 13 to allow blood flow to limb 17. Cuffs 10, 11 remain inflated to restrict blood flow to limbs 14, 15 respectively.

This routine can be repeatedly cycled as appropriate to the patient, for example, for the duration of the process of surgical removal of the blood clot from the blocked vessel, thereby enhancing blood flow to the collaterals until principal blood flow is restored.

The apparatus and method of the present invention does not prevent the simultaneous use of an aortic occlusion device or the administration of thrombolytic therapy. On the contrary, the present invention provides both a system which has standalone functionality to increase cerebral blood flow and a system which can be used to supplement existing treatments and therapies. In particular, use of the apparatus and method of the present invention does not preclude mechanical thrombectomy, which, under current medical practice, is the standard treatment for acute thromboembolic stroke. The method of the present invention can be continued during a mechanical thrombectomy in order to maintain cerebral circulation until the blood clot is removed. In this instance, a single cuff, ordinarily the cuff on the right lower limb, would be removed in order to obtain arterial access to perform mechanical thrombectomy.

In preferred embodiments, the apparatus further includes a feedback control arrangement, and preferably forms part of a system further comprising at least one cerebral blood flow assessment or monitoring apparatus, such that blood circulation to the brain is periodically or constantly assessed during operation of the apparatus.

The cerebral blood flow monitoring apparatus may, for example, involve the use of:
1. Ultrasound and transcranial Doppler, for assessing brain circulation continuously;
2. Near infra-red technology, for assessing the cerebral circulation continuously; or
3. CT or MR imaging modalities that can be performed at a single time point or repeatedly to optimise cerebral circulation.

By monitoring the cerebral circulation, individualised flow re-direction from the limbs to the brain can be achieved. For example it may be seen that, in certain patients, inflation of only the leg cuffs is sufficient for achieving maximal cerebral circulation and therefore inflation of the arm cuffs will add no further improvement to the cerebral circulation. In another instance it may be indicated that inflation of all the cuffs is required but that the cuff pressure required to achieve maximal cerebral circulation does not require complete occlusion of the arterial circulation to the limb i.e. 80% of systolic blood pressure re-directs the blood to the brain to the same degree as 100% of the systolic blood pressure, such that complete occlusion of the limb circulation is unnecessary.

Accordingly, the control module of the apparatus described above further includes a feedback module to which the cerebral blood flow monitoring apparatus is paired to provide regular or continuous monitoring of the cerebral circulation and automatically adjust the cuff inflation to maintain optimal cerebral circulation as close to normal as possible. Using continuous feedback it can be envisaged that in certain circumstances the starting cuff pressure may need to be increased over time to maintain optimal cerebral circulation. It will also be appreciated that in certain clinical scenarios, the blood flow returns to normal if, for example, an obstructive clot is lysed (destroyed) in which case, the feedback mechanism would detect a complete normalisation of the cerebral flow and deflate all of the cuffs.

Ideally the cerebral blood flow monitoring apparatus is able to detect the direction of flow in the cerebral vessels (anterograde or retrograde). Equally, the apparatus should, ideally, be able to measure the cerebral circulation in both the anterior and posterior circulation. In preferred embodiments, the cerebral blood flow apparatus is portable and, optionally, fully integrated with the control module. Nevertheless, a standalone apparatus couplable with the control module is also encompassed by the present invention.

Furthermore, it is envisaged that, over time and with use of the apparatus of the present invention, data collected from patients will be analysed such that, via automatic control and machine learning, an optimum cerebral circulation (flow direction, flow rate etc.) will be determined that will allow optimised care for individual patients. Accordingly, the control module of the apparatus of the present invention may further include data storage and communication functionality, for communicating with a central database of patient data.

Preferred embodiments of the present invention further include a heart rate monitor device for simultaneous monitoring of the heart rate, such as via an electrocardiogram (ECG). Simultaneous monitoring allows the control module to control inflation of the cuffs such that they are inflated with cardiac gating—in time with contraction of the heart (ventricles)—so that redirection of the blood occurs principally during the systolic phase. Partial deflation of the cuffs during the diastolic phase (ventricles relaxed and filling) could occur to allow blood flow to reach the limbs. By monitoring the heart rate and cerebral circulation and controlling the limb cuffs, optimal redirection of blood to the brain can be achieved. Inflation of the cuffs with the heart beat may or may not be required and in certain situations may not be feasible, for example in patients with atrial fibrillation where there is an irregular heartbeat.

It is further envisaged that the control module will include a control panel illustrating which of the cuffs are active cuffs, the activation of cuffs, in addition to information, in the preferred embodiments, regarding the cerebral circulation heart rate (ECG data). This will allow for easy identification of pertinent information and a user-friendly interface.

In preferred embodiments, the feedback control mechanism uses at least transcranial Doppler imaging of the intracranial cerebral arteries in order to control the cuff pressure of limb cuffs. A combination of transcranial ultrasound and additional imaging methods, for example textural analysis or near infra-red imaging of the brain, may also be used in conjunction with transcranial ultrasound.

Transcranial Doppler (TCD) ultrasonography provides a relatively inexpensive, noninvasive real-time measurement of blood flow characteristics and cerebrovascular hemodynamics within the basal arteries of the brain. The physiologic data obtained from these measurements are complementary to structural data obtained from various modes of currently available vascular imaging. TCD is the most convenient way to monitor vascular changes in response to interventions during acute cerebrovascular events at the bedside. Given the convenience of this tool as a diagnostic modality, its clinical and research applications will continue to increase in the many disorders of the cerebral vessel TCD ultrasonography is based on the principle of the Doppler effect. According to this principle, ultrasound waves emitted from the Doppler probe are transmitted through the skull and reflected by moving red blood cells within the intracerebral vessels. The difference in the frequency between the emitted and reflected waves, referred to as the "Doppler shift frequency," is directly proportional to the speed of the moving red blood cells (blood flow velocity).

Two types of TCD equipment are currently available: non-duplex (non-imaging) and duplex (imaging) devices. In non-duplex devices, the arteries are identified "blindly", based on the audible Doppler shift and the spectral display. Specific vessel identification is based on standard criteria, which includes the cranial window used, orientation of the probe, depth of sample volume, direction of blood flow, relationship to the terminal internal carotid artery, and response to various maneuvers such as the common carotid artery compression and eye opening and closing. The imaging B-mode transcranial color-coded duplex (TCCD) combines pulsed wave Doppler ultrasound with a cross-sectional view of the area of insonation, which allows identification of the arteries in relation to various anatomic locations. The color-coded Doppler also depicts the direction of the flow in relation to the probe (transducer) while recording blood flow velocities. In TCD, the angle of insonation is assumed <30 degrees (as close to zero as possible) to minimize the Doppler shift measurement error. However, in TCCD, the angle of insonation can be measured and used to correct the flow velocity measurement. More recently, a more advanced technology, called the power motion-mode TCD (PMD/TCD), has become available that provides multi-gate flow information simultaneously in the power M-mode display. It uses several overlapping sample volumes to simultaneously display flow signals. PMD/TCD appears to simplify handling of the TCD by facilitating the temporal window location and alignment of the incident signal to allow cerebral blood flow velocity recordings through multiple vessels.

The TCD examination is performed using a 2 MHz frequency ultrasound probe. The higher frequency probes used in extracranial Doppler studies are not applicable for intracranial measurements because higher frequency waves are not able to adequately penetrate through the skull. In addition to using a lower frequency probe, insonation of the cerebral arteries is only possible through thinner regions of the skull, termed acoustic windows. Therefore, familiarity with the anatomic location of cerebral arteries relative to the acoustic windows and blood flow velocities for the various arteries is critical for accurate blood flow measurements through the nonduplex mode. However, we envisage a device that is fully automated and therefore, the user (e.g. the paramedic) is not required to be trained in the use of TCD.

In general, four main acoustic windows have been described: (1) the transtemporal window (2) the transorbital window (3) the submandibular window, and (4) the suboccipital window. Although each window has unique advantages for different arteries and indications, for convenience, preferred embodiments of the present invention are primarily adapted to use the trans-temporal acoustic window to assess the cerebral arteries.

Specific arteries of the circle of Willis are identified using the following criteria: (1) relative direction of the probe within a specific acoustic window, (2) direction of blood flow relative to the probe, (3) depth of insonation, and (4) in difficult cases when it is not possible to differentiate the anterior from the posterior circulation, the blood flow response to carotid compression or vibration may be used.

Using the transtemporal acoustic window, the intracranial carotid artery (ICA) bifurcation can be identified at depths of 55 to 65 mm with simultaneous flow toward and away from the probe as the ICA bifurcation terminates in the anterior (flow away from the probe) and middle (flow toward the probe) cerebral arteries (ACA and MCA).

The ICA terminus is a convenient anatomic landmark to locate the vessels of the anterior circulation. The M1 segment of the MCA, viewed at depths of 35 to 55 mm, runs laterally and slightly anterior after its origin from the ICA. Flow in the M1 segment of the MCA should be toward the probe until the MCA bifurcation/trifurcation where flow normally becomes bidirectional. The ACA, which can be viewed at depths of 60 to 70 mm, begins coursing medially and then anteriorly after the ICA bifurcation. The ACA flow should normally be away from the probe.

The posterior cerebral artery (PCA) can also be insonated/scanned through the transtemporal window. In general, the PCA is found 1 to 2 cm posterior to the ICA bifurcation, but in the same plane as the circle of Willis. The PCA can be found posterior and deep to the ICA and MCA, at a depth of about 60 to 70 mm. Flow in the proximal PCA (P1 segment) is towards the probe and in the distal PCA (P2 segment) away from the probe. The PCA will always exhibit lower velocities than the MCA. It is important to note that in individuals where the PCA derives most of its flow from the ICA through a large posterior communicating artery (Pcom), the so-called fetal PCA configuration, the P1 segment is hypoplastic and may be very difficult to identify.

In addition to the direction of flow within the major arteries of the brain, TCD can also assess the waveform within these arteries and calculate the velocity of blood flow within the respective arteries. In this regard there is an extensive body of literature that has determined the normal waveform, direction and flow velocity within the different intra-cranial cerebral arteries.

The purpose of the advanced imaging, be it TCD, near infra-red or a combination of imaging modalities, is, in the first instance, to determine if an obstructive/partially obstructive clot is present. In order to do this the monitoring device would have two scanning probes that would ideally use the trans-temporal window to automatically determine the flow pattern and direction of flow in the intracranial arteries. The sequence would follow a similar, programmed and repeatable pattern—detection and direction of flow in the ICA, MCA, and ACA bilaterally. If there is absence of a normal flow pattern/signal in one of the arteries the system would then correlate with the flow from the contralateral side as well the flow in the arteries distal to the blockage. In these distal vessels there may be reversal of flow. This process would be entirely computerised and automated however, a display screen would show the flow patterns in the different arteries in order for operators to independently assess the flow pattern and the site of the thromboembolus. The system would also display the likely location of the blockage for the operator e.g. proximal MCA/M1 occlusion.

If there is no occlusion seen in the anterior circulation (ICA, MCA, or ACA bilaterally) the system would automatically proceed to assessing the posterior circulation territory and analyse the waveform and flow rate to determine if there is a possible occlusion at this site. Again, it would look at the flow and pattern in comparison to the flow in the anterior circulation and bilaterally in order to determine if there is an occlusion in the intracranial arteries for example. Again the device screen would demonstrate the waveform seen in each individual branch that is being assessed and whether a clot is present or not.

It is envisaged that, through machine learning, this process would increase in speed and accuracy over time and this information would be shared between all the devices via regular updates of the software.

If there is no evidence of clot (all vessels have a normal flow pattern, velocity and waveform) in any of the arteries the machine would recommend continued monitoring, but not therapy.

The collateral supply of the brain is highly variable and this collateral supply is essential in preserving the brain until definitive treatment with thrombolysis (clot-busting drugs) or thrombectomy (mechanical removal of the clot using surgery performed in dedicated hospitals) can be performed. It is well understood that the collateral supply can increase the time window in which these procedures can be performed and therefore, a greater number of people can undergo these treatments, as well a larger volume of brain tissue being preserved which will result in improved patient outcomes.

TCD can be used to assess this collateral supply. For example, as described earlier, the typical flow in the MCA is initially towards the probe (the M1 segment) and then becomes bidirectional and/or away from the probe (M2 branches distal to the bifurcation/trifurcation). Similarly, the velocity and flow patterns will be different in these different branches. If there is an occlusion in the M1 branch of the MCA then the flow will be, in the presence of good collaterals, reversed in the M2 branches i.e. it may flow towards the probe. There may also be a change in the flow pattern and velocity.

The TCD device after detecting the site of the blockage would then analyse the collateral flow pattern and commence augmentation. Augmentation of the collateral supply would involve inflating the limb cuffs of the apparatus of the present invention. Under continuous automated TCD monitoring of the collateral supply (e.g. the M2 branches in the presence of an M1 occlusion) the control system would initially recommend assessment of the blood pressure. This would be done by inflating a cuff, ideally that of the left arm, and calculating the systolic and diastolic blood pressure. Following the calculation of the systolic and diastolic pressure of the patient the device would inflate all the attached limb cuffs, of which there would typically be four, in a standard embodiment, but could be fewer in number where appropriate, for example for a patient having had a limb amputation. The control module then begins to inflate all the connected limb cuffs. At the same time as the cuffs are being inflated, the TCD assessment module would be monitoring the collateral supply of the brain for alterations in the blood flow and velocity. In particular the TCD assessment module would be assessing whether inflation of the cuffs caused an increase in the blood flow towards the blockage. The cuffs would be gradually inflated so as to allow accurate monitoring of the cerebral blood flow. If there is a sudden change in the blood flow pattern the device would rescan the proximal vessels (ICA, ACA and MCA or proximal basilar artery in the case of a posterior circulation stroke) as it may be that the clot dissolves spontaneously or after thrombolysis (which could be instituted after the machine detects the clot).

If the clot does not disintegrate, the flow in the collaterals would be continuously monitored as the pressure in the cuff increases. As long as the flow in the collaterals continues to improve, the cuffs will continue to inflate. An upper limit of cuff pressure would be approximately 20 mmHg (approximately 2666 Pa) above the systolic pressure. If there is no change whatsoever in the collateral flow during the cuff inflation, as recorded by the TCD scanning device, the cuffs would be deflated and the device would simply continue to monitor the cerebral blood flow.

The process would, for example, follow the following order:

1. The TCD monitoring device scans the cerebral blood vessels bilaterally to determine the site of the potential occlusion e.g. left M1 segment occlusion.
2. After determining the location of the clot, the TCD assesses the collateral circulation e.g. the left M2 vessels to determine if there is any collateral flow.
3. This information is continuously gathered and sent to the control module.
4. After determining the location of the clot and the collateral supply, the control module determines the blood pressure of the patient using the standard automated mechanism.
5. After the blood pressure has been calculated, and in the presence of a clot, the cuffs are inflated. During the inflation of the cuffs, the TCD monitoring part of the device continuously monitors the cerebral blood flow.
6. The machine continues to inflate the cuffs as long as the blood flow in the collateral arteries continues to improve e.g. better blood flow.
7. If there is no improvement in the collateral flow between the initial reading of the collateral flow and during the cuff inflation then the cuffs will be deflated.
8. If there is a sudden change in the blood flow pattern the TCD monitoring component of the device will reassess all the vessels to determine if there is still a clot present. If there is no evidence of a clot, the cuffs will be immediately deflated.
9. The TCD monitoring of the cerebral blood flow will continue throughout the time the cuffs are inflated.
10. The cuff inflation pressure may need to be continuously adjusted to optimise cerebral blood flow in the collaterals. For example, it may be found that cuff pressure needs to be increased after 30 minutes in order to maintain an optimal collateral blood flow.

The control module will display the actions being taken at each step and the likely location of the clot as well as the cuff pressure and the patient's blood pressure.

Other patterns of function are also suitable.

The cuffs and the TCD monitoring parts of the device can be retained in situ whilst the patient receives thrombolysis or undergoes a thrombectomy. However, in the case of a thrombectomy, a single cuff may need to be removed—which would typically be the right lower limb cuff. The monitoring of the collateral blood flow can continue until the clot has been dissolved/removed, at which point the TCD monitoring part of the device will recognise that the blood flow has been restored and the cuffs will be deflated.

The invention claimed is:

1. An apparatus for maintaining cerebral circulation in a patient above a baseline flow rate during treatment, the apparatus comprising:
   (a) a plurality of compression cuffs, each cuff being inflatable and deflatable and each cuff being positionable, in use, around a respective limb of a patient and inflatable to exert a pressure upon the limb sufficient to reduce limb blood flow below a point at which the cuff is positioned;
   (b) a control module to which the cuffs are attachable, the control module comprising fil a pump with which each cuff is in fluid communication, (ii) an imaging device adapted to determine where an occlusion is present in the cerebral circulation, and (iii) a valve arrangement associated with each cuff to control flow of fluid to and from each cuff, the control module being adapted to inflate and deflate each cuff independently of the others; and
   (c) a cerebral blood flow monitoring apparatus adapted to detect the baseline flow rate in the cerebral circulation and to repeatedly measure or continuously monitor flow rate in the cerebral circulation during treatment of the patient,
   wherein the control module is in operative communication with the cerebral blood flow monitoring apparatus, such that the control module is adapted to inflate one or more cuffs to reduce the respective limb blood flow below the point around the respective limb at which the inflated cuff or each inflated cuff is positioned and maintain inflation of the or each cuff for a predetermined period, to thereby elevate the cerebral circulation from the baseline flow rate to an increased flow rate, and thereafter control inflation of the plurality of cuffs to maintain the measured or monitored flow rate above the baseline flow rate during treatment, by reducing limb blood flow and augmenting cerebral circulation.

2. The apparatus as claimed in claim 1 wherein the predetermined period is at least about 6 hours.

3. The apparatus as claimed in claim 1 wherein the control module is configured to deflate each cuff sequentially for a plurality of release periods, the release periods being intermittent during the predetermined period.

4. The apparatus as claimed in claim 1 further comprising a sensor to determine the number of cuffs attached to the control module.

5. The apparatus as claimed in claim 1 wherein the cerebral blood flow monitoring apparatus is further adapted to detect flow direction in the cerebral circulation.

6. The apparatus as claimed in claim 1 wherein the cerebral blood flow monitoring apparatus is adapted to measure cerebral circulation in both anterior and posterior circulation.

7. The apparatus as claimed in claim 1 wherein the cerebral blood flow monitoring apparatus is adapted to determine cerebral blood flow rate in cerebral collateral arteries.

8. The apparatus as claimed in claim 1 wherein each cuff is independently inflatable to a determined pressure, which pressure may be the same as or different from each other cuff or all other cuffs.

9. The apparatus as claimed in claim 1 wherein each cuff comprises a blood flow sensor to determine whether, in use, blood is flowing through the limb of the patient adjacent the cuff.

10. The apparatus as claimed in claim 1 comprising four cuffs.

11. The apparatus as claimed in claim 1 wherein the control module is adapted to inflate each of the plurality of cuffs simultaneously to reduce limb blood flow to each limb simultaneously.

12. The apparatus as claimed in claim 1 wherein the control module is configured to control flow of fluid to and from the cuffs following a cyclical routine, each cycle of the routine comprising a series of steps of inflating all of the cuffs apart from one cuff to increase the cerebral circulation from the baseline flow rate to the increased flow rate and maintaining this configuration for a release period; and repeating this step for each of the plurality of cuffs in turn such that each cuff is deflated in turn and is maintained in a sufficiently-deflated state to allow blood flow to the respective limb whilst the other cuffs are configured in a sufficiently-inflated state to reduce limb blood flow.

13. The apparatus as claimed in claim 12 wherein the release period is between about one and twenty minutes.

14. The apparatus as claimed in claim 12 wherein the release period is at least about two minutes.

15. The apparatus as claimed in claim 12 wherein the release period is up to about five minutes.

16. A method for increasing a cerebral blood flow in a patient during treatment, the method comprising the steps of:
(i) detecting and measuring a baseline cerebral blood flow of the patient;
(ii) generating a reduced blood flow to each limb of the patient other than a first limb and allowing blood to flow to the first limb for a release period;
(iii) generating a reduced blood flow to the first limb and allowing blood flow to a second limb for the release period; and sequentially repeating for each limb the steps of allowing blood flow to one limb whilst generating a reduced blood flow to the other limbs, thereby increasing the cerebral circulation from a baseline flow rate to an increased blood flow rate;
(iv) monitoring the increased cerebral blood flow rate to determine an optimum treatment sequence, the optimum treatment sequence being a pattern of reducing and releasing limb blood flow that provides an increase in cerebral blood flow from the baseline cerebral blood flow; and
(v) using the optimum treatment sequence to maintain the cerebral blood flow at an increased level, relative to the baseline blood flow rate, throughout treatment of the patient.

17. A method for increasing a cerebral blood flow in a patient during treatment, the method comprising:
(i) detecting and measuring a baseline cerebral blood flow of the patient;
(ii) determining where an occlusion is present in a cerebral circulation of the patient using an imaging device;
(iii) generating a restricted limb blood flow to at least one limb of the patient using at least one cuff that is inflatable and deflatable;
(iv) detecting and measuring a treatment cerebral blood flow in response to the restricted limb blood flow and maintaining the restricted limb blood flow until the treatment cerebral blood flow is higher than the baseline cerebral blood flow; and
(v) monitoring the treatment cerebral blood flow throughout treatment of the patient and controlling inflation and deflation of the at least one cuff such that a treatment cerebral blood flow higher than the baseline blood flow rate is maintained throughout treatment of the patient.

18. The method as claimed in claim 17, further comprising generating a reduced limb flow to each limb of a patient for a predetermined period.

19. The method as claimed in claim 18, wherein blood is allowed to flow to each limb simultaneously for a plurality of release periods, the release periods being intermittent during the predetermined period.

* * * * *